United States Patent

Bigorra Llosas et al.

[11] Patent Number: 5,580,850
[45] Date of Patent: Dec. 3, 1996

[54] FOAMING DETERGENT MIXTURES

[75] Inventors: Joaquim Bigorra Llosas, Sabadell; Esther Prat Queralt, Alella; Oriol Ponsati Obiols, Barcelona, all of Spain

[73] Assignee: Henkel Kommanditgesellschaft auf Aktien, Duesseldorf, Germany

[21] Appl. No.: 374,767

[22] PCT Filed: Jul. 19, 1993

[86] PCT No.: PCT/EP93/01903

§ 371 Date: Mar. 23, 1995

§ 102(e) Date: Mar. 23, 1995

[87] PCT Pub. No.: WO94/02575

PCT Pub. Date: Feb. 3, 1994

[30] Foreign Application Priority Data

Jul. 27, 1992 [DE] Germany .................. 42 24 714.4

[51] Int. Cl.$^6$ .................. C11D 1/02; C11D 1/44; C11D 1/62; C11D 1/65
[52] U.S. Cl. .................. 510/504; 510/536; 510/495
[58] Field of Search .................. 252/547, 550, 252/174.17, 546, 542, 174.21

[56] References Cited

U.S. PATENT DOCUMENTS

| | | | |
|---|---|---|---|
| 4,554,097 | 11/1985 | Schebece et al. | 252/542 |
| 4,728,455 | 3/1988 | Rerek | 252/99 |
| 4,820,511 | 4/1989 | Hoeffkes et al. | 424/70 |
| 4,830,771 | 5/1989 | Ruback et al. | 252/8.8 |
| 4,840,738 | 6/1989 | Hardy et al. | 252/8.6 |
| 5,066,414 | 11/1991 | Chang | 252/8.8 |
| 5,266,690 | 11/1993 | McCurry, Jr. et al. | 536/18.6 |

FOREIGN PATENT DOCUMENTS

| | | |
|---|---|---|
| 0259678 | 3/1988 | European Pat. Off. . |
| 0295385 | 12/1988 | European Pat. Off. . |
| 9101295 | 2/1991 | WIPO . |
| 9310748 | 6/1993 | WIPO . |

OTHER PUBLICATIONS

J. Am. Oil. Chem. Soc. 65, 1977 (1988) (no month available).

"Kosmetische Färbemittel" of the Farbstoffkommission der Deutschen Forschungsgemeinschaft, published by Verlag Chemie, Weinheim, 1984, (no month available) pp. 81–106.

*Primary Examiner*—Erin M. Harriman
*Attorney, Agent, or Firm*—Wayne C. Jaeschke; John E. Drach; Henry E. Millson, Jr.

[57] ABSTRACT

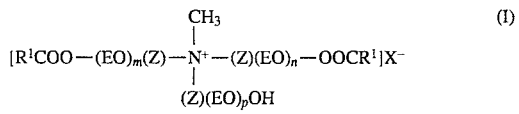

Described are detergent mixtures containing (a) quaternarized fatty-acid alkanolamine esters of formula (I), in which $R^1CO$ is an aliphatic acyl group with 6 to 22 carbon atoms and 0 or 1 double bonds, Z is an ethylene or isopropylene group, EO is a $CH_2CH_2O$— unit, (m+n+p) is a number from 1 to 10 and X is a halide, a methosulphate or an alkylphosphate anion, plus (b) other anionic, non-ionic and/or amphoteric or zwitterionic surfactants. Such mixtures have a high foaming power, are easily concentrated and have a long shelf life.

8 Claims, No Drawings

FOAMING DETERGENT MIXTURES

BACKGROUND OF THE INVENTION

1. Field of the Invention

This invention relates to foaming detergent mixtures containing quaternized fatty acid alkanolamine esters and other anionic, nonionic and/or amphoteric or zwitterionic surfactants, to compositions containing these mixtures and to the use of the mixtures for the production of laundry detergents, dishwashing detergents and cleaning products and hair-care and personal hygiene products.

2. Statement of Related Art

The production of surface-active compositions such as, for example, laundry detergents, dishwashing detergents and cleaning products, hair shampoos or foam baths normally involves the use of anionic, nonionic and/or amphoteric or zwitterionic surfactants which are responsible for the foaming, wetting and cleaning power of these products. The addition of cationic surfactants to such compositions is often desirable because these surface-active substances have a softening effect, a foam-stabilizing effect and, in some cases, even a microbicidal effect. Unfortunately, the reality is that cationic surfactants form insoluble complexes with anionic groups of other constituents present in the compositions. These insoluble complexes precipitate and can lead, for example, to fiber incrustations—a well-known phenomenon in the case of the alkylbenzenesulfonate/QUAT combination [J. Am. Oil. Chem. Soc. 65, 1977 (1988)].

Accordingly, the problem addressed by the present invention was to develop new detergent mixtures which would be free from the disadvantages mentioned above.

DESCRIPTION OF THE INVENTION

The present invention relates to foaming detergent mixtures containing a) quaternized fatty acid alkanolamine esters corresponding to formula (I):

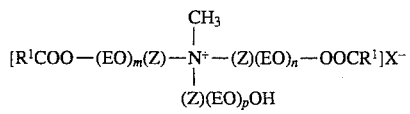

in which $R^1CO$ is an aliphatic acyl group containing 6 to 22 carbon atoms and 0 or 1 double bond, Z is an ethylene or isopropylene group, EO is a $CH_2CH_2O$ unit, (m+n+p) stands for numbers of 1 to 10 and X is a halide, methosulfate or alkylphosphate anion, and b) other anionic, nonionic and/or amphoteric or zwitterionic surfactants.

It has surprisingly been found that the detergent mixtures according to the invention show pronounced foaming power, favorable wetting properties, excellent washing and cleaning power and advantageous ecotoxicological and dermatological properties. More particularly, it has been found that quaternized fatty acid alkanolamine esters corresponding to formula (I) are highly compatible with anionic surfactants or surfactants containing anionic groups so that no insoluble salts or complexes are formed.

Quaternized fatty acid alkanolamine esters, so-called "esterquats", are known compounds which may be obtained by the relevant methods of preparative organic chemistry. One process for their production starts out from fatty acids and ethoxylated trialkanolamines which are esterified in the presence of acidic catalysts and a reducing agent while atmospheric oxygen is passed through and subsequently quaternized with dimethylsulfate [WO 91/01295, Pulcra]. The resulting products are technical mixtures essentially containing diesters and, in addition, monoesters and triesters.

Typical examples are fatty acid alkanolamine esters based on fatty acids containing 6 to 22 and, more particularly, 12 to 18 carbon atoms and 0 or 1 double bond with adducts of, on average, 1 to 10 and preferably 4 to 8 moles of ethylene oxide with triethanolamine or triisopropanolamine which are subsequently quaternized with methyl halides, dimethylsulfate or methylalkyl phosphates. It has proved to be of particular advantage to use difatty acid alkanolamine esters based on palmitic acid, stearic acid, elaidic acid and technical tallow fatty acid and adducts of, on average, 4 to 8 moles of EO with triethanolamine which are subsequently quaternized with methyl chloride or dimethylsulfate.

The foaming detergent mixtures according to the invention are obtained by combining the quaternized fatty acid alkanolamine esters with other anionic, nonionic and/or amphoteric or zwitterionic surfactants which are mentioned by way of example in the following:

a) Anionic Surfactants

Alkylbenzenesulfonates, alkanesulfonates, olefin sulfonates, alkylether sulfonates, glycerol ether sulfonates, α-methyl ester sulfonates, sulfofatty acids, alkylsulfates, fatty alcohol ether sulfates, glycerol ether sulfates, hydroxy mixed ether sulfates, monoglyceride (ether) sulfates, fatty acid amide (ether) sulfates, sulfosuccinates, sulfosuccinamates, sulfotriglycerides, ether carboxylic acids, alkyl oligoglucoside sulfates, alkyl(ether) phosphates, protein fatty acid condensates.

b) Nonionic Surfactants fatty alcohol polyglycol ethers, alkylphenol polyglycol ethers, fatty amine polyglycol ethers, fatty acid amide polyglycol ethers, fatty acid polyglycol esters, alkoxylated triglycerides, alkyl oligoglycosides, sugar esters, sorbitan esters, polysorbates, polyol fatty acid esters, amine oxides, fatty acid alkanolamides, alkyl lactams, fatty acid N-alkyl glucamides.

c) Amphoteric or Zwitterionic Surfactants

Alkylamidobetaines, aminopropionates, aminoglycinates, imidazolinium betaines and sulfobetaines.

The quaternized fatty acid alkanolamine esters may be present in the detergent mixtures according to the invention in quantities of 0.1 to 90% by weight, preferably in quantities of 5 to 80% by weight and more preferably in quantities of 15 to 50% by weight, based on the solids content of the mixtures.

Typical examples of foaming detergent mixtures with particularly advantageous properties are mentioned in the following:

1% by weight of a quaternized distearic acid triethanolamine 4EO ester quaternized with dimethylsulfate in admixture with 40% by weight of a C$_{12/14}$ coconut oil fatty alcohol 2EO ethersulfate Na salt (water ad 100% by weight);

5% by weight of a quaternized ditallow fatty acid triethanolamine 6EO ester quaternized with dimethylsulfate in admixture with 40% by weight of a C$_{12/14}$ cocoalkyl oligoglucoside (water ad 100% by weight); 10% by weight of a quaternized dielaidic acid triethanolamine 8EO ester quaternized with methyl chloride in admixture with 25% by weight of an imidazolinium betaine (water ad 100% by weight).

To produce the detergent mixtures according to the invention it is sufficient to mix and, if necessary, homogenize the components, optionally while heating to a temperature of 30° to 40° C. It is possible in this regard to start out from concentrates which are diluted with water to an in-use concentration of 1 to 50% by weight and preferably 15 to 30% by weight or to use dilute water-based starting materials from the outset. In either case, the operation involved is purely mechanical, i.e. does not involve a chemical reaction.

The present invention also relates to:

Powder-form universal detergents containing 10 to 30% by weight, based on the detergent, of a mixture of quaternized fatty acid esters corresponding to formula (I), anionic, nonionic and/or amphoteric or zwitterionic surfactants and also typical auxiliaries and additives.

Liquid universal detergents containing 10 to 70% by weight, based on the detergent, of a mixture of quaternized fatty acid alkanolamine esters corresponding to formula (I), anionic, nonionic and/or amphoteric or zwitterionic surfactants and also typical auxiliaries and additives.

Liquid light-duty detergents containing 10 to 50% by weight, based on the detergent, of a mixture of quaternized fatty acid alkanolamine esters corresponding to formula (I), anionic, nonionic and/or amphoteric or zwitterionic surfactants and also typical auxiliaries and additives.

Manual dishwashing detergents containing 10 to 50% by weight, based on the detergent, of a mixture of quaternized fatty acid alkanolamine esters corresponding to formula (I), anionic, nonionic and/or amphoteric or zwitterionic surfactants and also typical auxiliaries and additives.

Liquid cleaners and disinfectants containing 10 to 30% by weight, based on the cleaner/disinfectant, of a mixture of quaternized fatty acid alkanolamine esters corresponding to formula (I), anionic, nonionic and/or amphoteric or zwitterionic surfactants and also typical auxiliaries and additives.

Hair shampoos containing 10 to 30% by weight, based on the shampoo, of a mixture of quaternized fatty acid alkanolamine esters corresponding to formula (I), anionic, nonionic and/or amphoteric or zwitterionic surfactants and also typical auxiliaries and additives.

Hair rinses containing 10 to 30% by weight, based on the hair rinse, of a mixture of quaternized fatty acid alkanolamine esters corresponding to formula (I), anionic, nonionic and/or amphoteric or zwitterionic surfactants and also typical auxiliaries and additives.

Foam baths containing 10 to 30% by weight, based on the foam bath, of a mixture of quaternized fatty acid alkanolamine esters corresponding to formula (I), anionic, nonionic and/or amphoteric or zwitterionic surfactants and also typical auxiliaries and additives.

Laundry detergents based on the detergent mixtures according to the invention may contain, for example, builders, salts, bleaching agents, bleach activators, optical brighteners, redeposition inhibitors, solubilizers and enzymes as auxiliaries and additives.

Typical builders are sodium aluminium silicates (zeolites), phosphates, phosphonates, ethylenediamine tetraacetic acid, nitrilotriacetate, citric acid and/or polycarboxylates. Suitable salts or diluents are, for example, sodium sulfate, sodium carbonate or sodium silicate (waterglass). Typical individual examples of other additives are sodium borate, starch, sucrose, polydextrose, TAED, stilbene compounds, methyl cellulose, toluene sulfonate, cumene sulfonate, long-chain soaps, silicones, mixed ethers, lipases and proteases.

Hair shampoos, hair lotions or foam baths based on the detergent mixtures according to the invention may contain, for example, emulsifiers, oil components, fats and waxes, thickeners, superfatting agents, biogenic agents, film formers, fragrances, dyes, pearlescers, preservatives and pH regulators as auxiliaries and additives.

Typical oil components are such substances as paraffin oil, vegetable oils, fatty acid esters, squalene and 2-octyldodecanol. Suitable fats and waxes are, for example, spermaceti, beeswax, montan wax, paraffin and cetostearyl alcohol. Superfatting agents may be selected from such substances as, for example, polyethoxylated lanolin derivatives, lecithin derivatives and fatty acid alkanolamides, the fatty acid alkanolamides also serving as foam stabilizers. Suitable thickeners are, for example, polysaccharides, more particularly xanthan gum, guar guar, agar agar, alginates and tyloses, carboxymethyl cellulose and hydroxyethyl cellulose, also relatively high molecular weight polyethylene glycol monoesters and diesters of fatty acids, polyacrylates, polyvinyl alcohol and polyvinyl pyrrolidone and electrolytes, such as sodium chloride and ammonium chloride. In the context of the invention, biogenic agents are, for example, plant extracts, protein hydrolyzates and vitamin complexes. Typical film formers are, for example, polyvinyl pyrrolidone, vinyl pyrrolidone/vinyl acetate copolymers, polymers of the acrylic acid series, quaternary cellulose derivatives and similar compounds. Suitable preservatives are, for example, formaldehyde solution, p-hydroxybenzoate or sorbic acid. Suitable pearlescers are, for example, glycol distearic acid esters, such as ethylene glycol distearate, and also fatty acid monoglycol esters. The dyes used may be selected from any of the substances which are permitted and suitable for cosmetic purposes, as listed for example in the publication "Kosmetische Färbemittel" of the Farbstoffkommission der Deutschen Forschungsgemeinschaft, published by Verlag Chemie, Weinheim, 1984, pages 81–106. These dyes are typically used in concentrations of 0.001 to 0.1% by weight, based on the mixture as a whole.

Commercial Applications

The detergent mixtures according to the invention are distinguished by excellent washing and cleaning power, hair-conditioning and fabric-conditioning properties, an antistatic effect on hair and fibers and an improvement in combability and also by high ecotoxicological compatibility.

Accordingly, the present invention also relates to their use for the production of laundry detergents, dishwashing detergents and cleaning products and also hair-care and personal hygiene products in which they may be present in quantities of 1 to 50% by weight and preferably in quantities of 10 to 30% by weight, based on the particular product.

The following Examples are intended to illustrate the invention without limiting it in any way.

Examples

I. Surfactants used

A) Quaternized fatty acid alkanolamine esters corresponding to formula (I)[1]

[1] Commercial products of Pulcrra S.A. Barcelona, Spain

|    | $R^1CO$ | Z | (m + n + p) | $X^-$ |
| --- | --- | --- | --- | --- |
| A1 | $C_{17}H_{35}CO$ | $CH_2CH_2$ | 4 | $CH_3SO_4^-$ |
| A2 | $C_{17}H_{35}CO$ | $CH_2CH_2$ | 6 | $CH_3SO_4^-$ |
| A3 | $C_{17}H_{35}CO$ | $CH_2CH_2$ | 8 | $CH_3SO_4^-$ |

B) $C_{12/14}$ coconut oil fatty alcohol 2EO sulfate Na/mg salt[2] Texapon® NSO

C) $C_{12/14}$ coconut oil fatty alcohol diethanolamide[2] Comperlan® COD

D) $C_{12/14}$ coconut oil fatty acid amidobetaine[2] Dehyton® K

[2] Commercial products of Henkel KGaA, Düsseldorf, FRG

II. Results of performance tests—thickenability

The thickening effect of sodium chloride on mixtures containing fatty alcohol ethersulfate, fatty acid alkanolamide and optionally esterquats was measured in a Brookfield RVT viscosimeter (spindle 2–7, 10 r.p.m.) at 20° C. The results are set out in Table 1.

TABLE 1

Viscosity on addition of x % of sodium chloride
Percentages as % by weight

| | Formulation* | | | | | | Viscosity (1000 cps) | | | | |
|---|---|---|---|---|---|---|---|---|---|---|---|
| | A1 | A2 | A3 | B | C | D | | | | | |
| Ex. | % | % | % | % | % | % | 2% | 3% | 4% | 5% | 6% |
| 1 | 1 | — | — | 37 | 2 | — | 1 | 15 | 33 | 6 | 1 |
| 2 | — | 1 | — | 37 | 2 | — | 2 | 11 | 16 | 4 | 1 |
| 3 | — | — | 1 | 37 | 2 | — | 2 | 11 | 16 | 14 | 4 |
| 4 | 1 | — | 1 | 37 | — | 8 | 5 | 20 | 29 | 13 | 1 |
| 5 | — | 1 | — | 37 | — | 8 | 5 | 27 | 32 | 18 | 2 |
| 6 | — | — | 1 | 37 | — | 8 | 5 | 27 | 32 | 19 | 2 |
| C1 | — | — | — | 37 | 2 | — | 1 | 5 | 14 | 20 | 17 |
| C2 | — | — | — | 37 | — | 8 | 1 | 18 | 27 | 38 | 33 |

*Water ad 100% by weight

Storage behavior

The various formulations were stored at 5, 20 and 40° C. and evaluated for viscosity after 15 days and 30 days. The results are set out in Table 2:

TABLE 2

Storage behavior at various temperatures
Percentages as % by weight

| | Formulation* | | | | | | Viscosity (cps) | | |
|---|---|---|---|---|---|---|---|---|---|
| | A2 | A3 | B | C | D | t | | | |
| Ex. | % | % | % | % | % | d | 5° C. | 20° C. | 40° C. |
| 7 | 1 | — | 37 | 2 | — | 0 | 3000 | 3050 | 3400 |
| | 1 | — | 37 | 2 | — | 15 | 3050 | 3100 | 5100 |
| | 1 | — | 37 | 2 | — | 30 | 3000 | 3075 | 6600 |
| 8 | — | 1 | 37 | 2 | — | 0 | 3950 | 4050 | 3200 |
| | — | 1 | 37 | 2 | — | 15 | 3900 | 4100 | 5200 |
| | — | 1 | 37 | 2 | — | 30 | 3700 | 4000 | 6700 |
| 9 | 1 | — | 37 | — | 8 | 0 | 3050 | 2800 | 2850 |
| | 1 | — | 37 | — | 8 | 15 | 3100 | 2950 | 3600 |
| | 1 | — | 37 | — | 8 | 30 | 3050 | 3000 | 4600 |
| 10 | — | 1 | 37 | — | 8 | 0 | 3450 | 3450 | 3500 |
| | — | 1 | 37 | — | 8 | 15 | 3450 | 3050 | 4400 |
| | — | 1 | 37 | — | 8 | 30 | 3450 | 3055 | 5000 |
| C3 | — | — | 37 | 2 | — | 0 | 2800 | 2850 | 3000 |
| | — | — | 37 | 2 | — | 15 | 2950 | 2875 | 4000 |
| | — | — | 37 | 2 | — | 30 | 2450 | 2870 | 4400 |
| C4 | — | — | 37 | — | 8 | 0 | 3050 | 3900 | 3000 |
| | — | — | 37 | — | 8 | 15 | 3100 | 3950 | 3050 |
| | — | — | 37 | — | 8 | 30 | 3050 | 3900 | 3500 |

*Water ad 100% by weight

Foaming power

The foaming power of the 0.5% by weight formulations was determined in a ROSS-MILES foam generating apparatus using water with a hardness of 16° d. The height of the basic foam and also the foam collapse after 1, 3 and 5 minutes were measured. The results are set out in Table 3.

TABLE 3

Foaming capacity
Percentages as by weight

| | Formulation* | | | | | Foam height (ml) | | | |
|---|---|---|---|---|---|---|---|---|---|
| | A2 | A3 | B | C | D | | | | |
| Ex. | % | % | % | % | % | 0' | 1' | 3' | 5' |
| 11 | 1 | — | 37 | 2 | — | 110 | 110 | 100 | 100 |
| 12 | — | 1 | 37 | 2 | — | 120 | 110 | 100 | 100 |
| 13 | 1 | — | 37 | — | 8 | 110 | 105 | 100 | 100 |
| 14 | — | 1 | 37 | — | 8 | 110 | 105 | 100 | 100 |
| C5 | — | — | 37 | 2 | — | 110 | 100 | 90 | 90 |
| C6 | — | — | 37 | — | 8 | 110 | 110 | 100 | 90 |

*Water ad 100% by weight

What is claimed is:

1. Foaming detergent mixture consisting essentially of (a) from about 15 to about 50% by weight of at least one quaternized fatty acid alkanolamine ester of the formula (I):

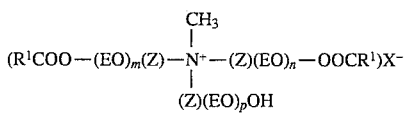

wherein $R^1CO$ is an aliphatic acyl group having from about 6 to about 22 carbon atoms and 0 or 1 double bond, Z is an ethylene or isopropylene group, EO is a $CH_2CH_2O$ unit, m, n, and p are numbers having values such that m+n+p is equal to from 1 to 10 and x is a halide, methosulfate or alkylphosphate anion; and (b) an anionic surfactant.

2. The foaming detergent mixture of claim 1 wherein said anionic surfactant is selected from the group consisting of an alkylbenzenesulfonate, an alkanesulfonate, an olefin sulfonate, an alkylether sulfonate, a glycerol ether sulfonate, an α-methyl ester sulfonate, an sulfofatty acid, an alkylsulfate, a fatty alcohol ether sulfate, a glycerol ether sulfate, an hydroxy mixed ether sulfate, a monoglyceride(ether)sulfate, a fatty acid amide(ether)sulfate, a sulfosuccinate, a sulfosuccinamate, a sulfotriglyceride, an ether carboxylic acid, an alkyl oligoglucoside sulfate, an alkyl(ether)phosphate and a protein fatty acid condensate.

3. The foaming detergent mixture of claim 1 wherein said quaternized fatty acid alkanolamine ester is quaternized distearic acid triethanolamine 4EO ester quaternized with dimethylsulfate and said anionic surfactant is present at about 40% by weight and is a $C_{12/14}$ coconut oil fatty alcohol 2EO ethersulfate Na salt and wherein said mixture further comprises water.

4. The foaming detergent mixture of claim 1 wherein said quaternized fatty acid alkanolamine ester is quaternized ditallow fatty acid triethanolamine 6EO ester quaternized with dimethylsulfate.

5. The foaming detergent mixture of claim 1 wherein said quaternized fatty acid alkanolamine ester is quaternized dielaidic acid triethanolamine 8EO ester quaternized with methyl chloride.

6. The foaming of claim 1 wherein in formula 1 the $R^1CO$ group has from 12 to 18 carbon atoms and the sum of m+n+p is equal to from 4 to 8.

7. The foaming of claim 1 wherein the at least one compound of formula 1 is at least one quaternized difatty acid alkanolamine ester based on palmitic acid, stearic acid, elaidic acid, or technical tallow fatty acid; and m+n+p is equal to 4 to 8.

8. The foaming of claim 7 wherein the quaternized difatty acid alkanolamine ester is quaternized with methyl chloride or dimethylsulfate.

* * * * *